United States Patent [19]

Kosonen

[11] 4,351,326
[45] Sep. 28, 1982

[54] COPPER WIRE FOR INTRAUTERINA CONTRACEPTIVE DEVICES AND A METHOD FOR MANUFACTURING THE SAME

[75] Inventor: Ahti A. Kosonen, Pori, Finland

[73] Assignee: Outokumpu Oy, Helsinki, Finland

[21] Appl. No.: 193,484

[22] Filed: Oct. 3, 1980

[30] Foreign Application Priority Data

Apr. 2, 1980 [FI] Finland ............................ 801073

[51] Int. Cl.$^3$ ..................... B22F 3/00; A61F 5/46
[52] U.S. Cl. ............................. 128/130; 428/602; 428/607; 428/608
[58] Field of Search ............... 128/130; 428/602, 607, 428/608

[56] References Cited

U.S. PATENT DOCUMENTS

| | | | |
|---|---|---|---|
| 2,434,992 | 1/1948 | Durst | 428/602 |
| 3,181,935 | 5/1965 | Coad | 428/607 |
| 3,703,896 | 11/1972 | Nuwayser | 128/130 |
| 3,877,885 | 4/1975 | Sexton | 428/607 |
| 4,117,838 | 10/1978 | Hasson | 128/130 |
| 4,198,966 | 4/1980 | Kaivola | 128/130 |

FOREIGN PATENT DOCUMENTS

| | | | |
|---|---|---|---|
| 2431286 | 3/1980 | France | 128/130 |
| 156146 | 4/1962 | U.S.S.R. | 428/607 |

*Primary Examiner*—Brooks H. Hunt
*Attorney, Agent, or Firm*—Brooks, Haidt, Haffner & Delahunty

[57] ABSTRACT

A copper wire for intrauterine contraceptive devices is disclosed as having a core wire of a flexible tough metal nobler than copper and a copper coating fixed on the core wire by means of a thin diffusion layer.

1 Claim, No Drawings

COPPER WIRE FOR INTRAUTERINA CONTRACEPTIVE DEVICES AND A METHOD FOR MANUFACTURING THE SAME

BACKGROUND OF THE INVENTION

The present invention relates to copper wire for intrauterine contraceptive devices, the copper wire having a core wire owing corrosion-resistivity against uterine fluids, and to a method for manufacturing such copper wire.

It has been observed that, due to the dissolution in the uterus, copper wire often corrodes locally, and consequently the wire fragmentates and disintegrates before all of the copper has dissolved. This decreases the effective using time of intrauterine devices. In the publication "Fertility and Sterility", 30 (1) (1978) 59–65, it is pointed out that in the copper T-200 (manufactured by Hallmark Plastics Inc, U.S.A.) devices investigated, fragmentation was detected in one case after only 8 months of use. Previous studies [Population Council's Report (NDA), Wire Fragmentation, 1973] have shown severe corrosion and fragmentation in the copper wire of a intrauterine device after only 5 months of use.

In all present available intrauterine copper devices the problem is the reduced using time due to the corrosion and fragmentation of the copper wires used in them. It has been suggested that copper can be deposited electrolytically on a stainless wire, in order to avoid described disadvantage. In this case, the actual wire consists of stainless steel. Stainless, acid-resistant steel or other such kind of alloys are, however, quite rigid and thus not suitable for use in intrauterine devices. Furthermore, electrolytically coated copper may flake when corrosion reaches the steel. Furthermore, it can be assumed that, owing to electrochemical difference in voltage between the steel and the copper, the corrosion of copper is accelerated when the core is exposed.

SUMMARY OF THE INVENTION

The present invention provides a wire for intrauterine devices, the wire having a corrosion-resistant core wire of some ductile metal nobler than copper, a copper coating being fixed on this core wire with the aid of a thin diffusion layer.

The nobler metal to be used is preferably silver, gold, or platinum, especially silver.

These metals also have the advantage that they can easily be deformed together with copper, and thus a method other than the electrolytic method can be used for joining the metals.

The method of the invention for manufacturing copper wire for intrauterine devices is characterized in that a wire of some ductile metal nobler than copper is fitted inside a copper tube, and the two metals are joined together by working and annealing in order to produce a thin diffusion layer on the interface between the nobler metal and copper.

The copper tube, with a thin wall, is made from medical grade copper either by extrusion or by some other known tube-manufacturing method.

DESCRIPTION OF THE PREFERRED EMBODIMENTS

The silver rod is made from 99.99-percent silver by casting, extruding, forging, or some other known method, and it is drawn out to a suitable, relatively thick dimension, preferably approx. 10 mm. Thereafter, the thick-walled copper tube is reduced so that its bore diameter is suitably somewhat greater than the diameter of the silver rod, and the said silver rod is passed inside the tube. The thickness of the tube and the silver rod have been determined so as to correspond to the cross-sectional proportions in the final dimension. Thereafter, the copper and the silver rod are drawn together through several successive drawing stages and drawing rings, whereby the copper is pressed tightly onto the silver. However, this mechanical joint is not sufficient, and therefore the material is treated by so-called diffusion annealing, whereby, at a suitable temperature and within a suitable time, a slight diffusion between copper and silver is achieved. It should be noted that the diffusion layer must be very thin, since the copper-silver alloy dissolves in the uterine fluids, and a silver core with a thick layer of silver-copper alloy would dissolve and become fragmented. After the diffusion annealing, or several diffusion annealings if necessary, the material is drawn out to its final thickness, which is often 0.2–0.4 mm. The wire can be used as such or soft annealed, in which case excessive diffusion should again be avoided. In this case normal resistance annealing is the most advantageous form of annealing; since owing to the short time it requires, diffusion cannot be produced. Thereafter the wire is ready for use for the manufacture of intrauterine devices.

Another suitable manufacturing method is to join the said materials together, at a suitable ratio, by hydrostatic extrusion because in this method so low a temperature can be used that excessive diffusion cannot be produced.

Copper wire manufactured in accordance with the invention was tested in use in intrauterine devices called Nova T. Since the dissolving of copper is very slow, not until now has it been possible to obtain reliable proofs of the fact that the wire works as described above. Thus, after trial use of approx. 4 years, devices have been seen in which the copper has dissolved and the silver core has been exposed. No signs of dissolving have been detected in the core, and so the copper wire according to the invention is usable.

The following example illustrates the manufacture of a copper wire according to the invention.

EXAMPLE

In accordance with the above, a tube was made from pure copper by pressing it to a thickness of 46/30 mm (outer diameter/inner diameter), and thereafter it was drawn out to a diameter of 22/9. A silver rod was manufactured by casting it 12 mm thick, and it was drawn out to 8.5 mm. The silver rod was passed inside the copper tube with a bore diameter of 9 mm, and they were drawn together until the outer diameter was 18 mm, whereafter an annealing was carried out at 500° C. for approx. 20 min. 500° C. was selected for the reason that diffusion between copper and silver does not occur at this temperature. Thereafter the material was drawn out to 12.8 mm, and an annealing at 500° C. for 20 min was carried out. Furthermore, it was drawn out to 8 mm, and thereafter a diffusion annealing at 600° C. was carried out for 20 min. Thereafter the wire was reduced to a diameter of 0.3 mm by two drawing operations in series, using resistance annealing for softening during the series drawing. In resistance annealing there is not enough time for the above-described diffusion to take place.

I claim:
1. A method for preventing conception comprising placing in the uterus an intrauterine contraceptive device having a wire form a corrosion-resistant core wire of some ductile metal nobler than copper and a coating of copper fixed onto the core wire by means of a thin diffusion layer.

* * * * *

UNITED STATES PATENT AND TRADEMARK OFFICE
CERTIFICATE OF CORRECTION

PATENT NO. : 4,351,326
DATED : September 28, 1982
INVENTOR(S) : Ahti A. Kosonen

It is certified that error appears in the above—identified patent and that said Letters Patent is hereby corrected as shown below:

Column 3:

Claim 1, line 4:

"a wire form a" should read --a wire formed of a--.

Signed and Sealed this

Tenth Day of May 1983

[SEAL]

Attest:

GERALD J. MOSSINGHOFF

Attesting Officer  Commissioner of Patents and Trademarks